United States Patent [19]
Arhancet et al.

[11] Patent Number: 5,773,674
[45] Date of Patent: Jun. 30, 1998

[54] COMPOSITIONS AND METHODS FOR INHIBITING VINYL AROMATIC MONOMER POLYMERIZATION

[75] Inventors: Graciela B. Arhancet, Katy; Inge K. Henrici, Spring, both of Tex.

[73] Assignee: BetzDearborn Inc., Trevose, Pa.

[21] Appl. No.: 775,555

[22] Filed: Dec. 31, 1996

Related U.S. Application Data

[62] Division of Ser. No. 489,904, Jun. 12, 1995, Pat. No. 5,648,573.

[51] Int. Cl.⁶ .................................................. C07C 7/20
[52] U.S. Cl. ................................. 585/5; 585/4; 585/12; 585/24; 252/403; 252/404
[58] Field of Search .................................... 252/403, 404; 585/4, 5, 12, 24

[56] References Cited

U.S. PATENT DOCUMENTS

| | | |
|---|---|---|
| 2,388,041 | 10/1945 | Craig . |
| 2,394,756 | 2/1946 | Dreisbach . |
| 2,965,685 | 12/1960 | Campbell . |
| 3,674,651 | 7/1972 | Otsuki et al. ................................. 203/8 |
| 4,105,506 | 8/1978 | Watson ......................................... 203/9 |
| 4,237,326 | 12/1980 | Fuga et al. .................................... 585/4 |
| 4,409,408 | 10/1983 | Miller ........................................... 585/4 |
| 4,466,905 | 8/1984 | Butler et al. .............................. 252/403 |
| 4,720,566 | 1/1988 | Martin ...................................... 558/306 |
| 4,774,374 | 9/1988 | Abruscato et al. ......................... 585/24 |
| 5,371,280 | 12/1994 | Haramaki et al. .......................... 562/26 |
| 5,396,004 | 3/1995 | Arhancet et al. ............................ 585/5 |
| 5,426,257 | 6/1995 | Arhancet ..................................... 585/5 |
| 5,446,220 | 8/1995 | Arhancet ..................................... 585/5 |
| 5,470,440 | 11/1995 | Arhancet ..................................... 203/9 |
| 5,562,863 | 10/1996 | Arhancet ..................................... 585/5 |

FOREIGN PATENT DOCUMENTS

| | | |
|---|---|---|
| 163428 | 6/1976 | Czechoslovakia . |
| 240297 | 10/1987 | European Pat. Off. . |
| 50-21117 | 8/1976 | Japan . |
| 86-317087 | 7/1982 | U.S.S.R. . |

*Primary Examiner*—Elizabeth D. Wood
*Attorney, Agent, or Firm*—Alexander D. Ricci; Philip H. Von Neida

[57] ABSTRACT

The polymerization of a vinyl aromatic monomer such as styrene is inhibited by the addition of a composition of a benzoquinone derivative and a hydroxylamine compound.

5 Claims, No Drawings

COMPOSITIONS AND METHODS FOR INHIBITING VINYL AROMATIC MONOMER POLYMERIZATION

This is a divisional of application Ser. No. 08/489,904 filed Jun. 12, 1995, now U.S. Pat. No. 5,648,573.

FIELD OF THE INVENTION

The present invention relates to compositions and methods for inhibiting the unwanted polymerization of vinyl aromatic monomer compounds. More particularly, the present invention relates to a composition comprising a benzoquinone derivative and a hydroxylamine compound having the ability to inhibit polymerization of vinyl aromatic monomer compounds.

BACKGROUND OF THE INVENTION

Common industrial methods for producing styrene typically include separation and purification processes such as distillation to remove unwanted impurities. Unfortunately, purification processes carried out at elevated temperatures result in an increased rate of undesired polymerization. Distillation is generally carried out under vacuum to minimize loss of monomer. The presence of oxygen, although virtually excluded in styrene distillation, will also promote polymerization of the monomer.

This polymerization results not only in loss of desired monomer end-product, but also in the loss of production efficiency caused by polymer formation and/or agglomeration of polymer on process equipment. Thermal polymerization, which typically occurs during distillation, of styrene monomer results in the formation of normal (i.e., linear) polymer. This resulting polystyrene polymer is characterized by its glassy and transparent appearance and its solubility in the styrene monomer and many organic solvents.

The compounds generally used commercially to inhibit polymerization of vinyl aromatic monomers are of the dinitrophenol family. For example, U.S. Pat. No. 4,105,506, Watson et al. teaches the use of 2.6-dinitro-p-cresol as a polymerization inhibitor for vinyl aromatic compounds. U.S. Pat. No. 4,466,905, Butler et al. teaches that a combination of 2,6-dinitro-p-cresol and p-phenylenediamines will inhibit polymerization in a distillation column when oxygen is present. U.S. Pat. No. 4,774,374, Abruscato et al. teaches compositions for inhibiting the polymerization of vinyl aromatic compounds. The composition employs an oxygenated product of the reaction of an N-aryl-N'-alkyl-p-phenylenediamine with oxygen. U.S. Pat. No. 4,720, 566, Martin teaches the use of a hydroxylamine compound and a phenyl-p-phenylenediamine compound to inhibit the polymerization of acrylonitrile in a quench tower.

U.S. Pat. No. 3,674,651, Otsuki et al. teaches the use of benzoquinone for inhibiting the polymerization of acrylic acid. U.S. Pat. No. 5,396,004, Arhancet et al. teaches the use of a combination of a phenylenediamine compound and a hydroxylamine compound, preferably a hydroxyalkylhydroxylamine, to inhibit the polymerization of vinyl aromatic compounds during processing.

Czechoslovakia Patent No. 163,428 teaches a method for stabilizing styrene and divinylbenzene utilizing 2,4-dinitroorthocresol and diethylhydroxylamine. European Patent Application 240 297 teaches the use of this combination to inhibit polymerization of styrene. The use of diethylhydroxylamine however is problematic in styrene purification processes as it has a boiling point of 125° C. to 130° C. at 760 mm Hg that is similar to styrene and can be carried over with the styrene during processing.

A variety of inhibitor compositions have been employed in styrene and other vinyl aromatic monomers to inhibit undesired polymerization. Agents that have been used include sulfur, p-benzoquinone, phenylene-diamines, tert-butyl pyrocatechol, phenothiazine, hydroxylamines and hindered phenols. However, many of these compounds present disadvantages such as high toxicity, instability, explosive hazard at elevated temperature and insufficient efficacy under processing conditions (i.e., inhibitor requires oxygen to be effective). The present inventors have discovered a novel composition which acts synergistically to inhibit vinyl aromatic monomer polymerization while avoiding these problems associated with the known inhibitors.

DETAILED DESCRIPTION OF THE INVENTION

The present invention relates to compositions and methods for inhibiting the polymerization of vinyl aromatic monomer compounds comprising adding to the monomers a combination of a benzoquinone derivative and a hydroxylamine compound.

The compositions of the present invention are effective at inhibiting polymerization of vinyl aromatic monomers under processing conditions. These processing conditions include but are not limited to preparation, purification, distillation and vacuum distillation processes. The compositions of the present invention are effective in both processes where oxygen is present and under oxygen-free processing conditions. The term "oxygen free" is meant to define the substantially oxygen free conditions under which vinyl aromatic monomers, particularly styrene are often processed. These conditions, exemplified by distillation and purification processes generally have less than 2 parts per million parts of oxygen present and preferably less than 1 part of oxygen per million parts styrene.

The vinyl aromatic monomers that are treated by the compositions of the present invention include but are not limited to styrene, bromostyrene, divinylbenzene, and a-methylstyrene. The compositions of the present invention are particularly efficacious at inhibiting the polymerization of styrene monomer.

The benzoquinone derivatives useful in the present invention generally have the formula

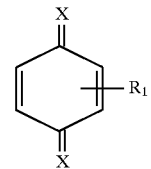

wherein X is N-R or O;R is H, phenyl or a $C_1$ to $C_7$ alkyl group; and $R_1$ is a $C_1$ to $C_7$ alkyl. The preferred benzoquinone derivatives are tert-butyl-benzoquinone and N,N-dimethylindoaniline (phenol blue).

The hydroxylamine compounds useful in the present invention generally have the formula

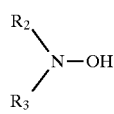

wherein $R_2$ and $R_3$ are the same or different and are hydrogen, alkyl, aryl, alkaryl, aralkyl, or hydroxyalkyl groups and preferably have about three to about twenty carbon atoms. The preferred hydroxylamine compound is bis(hydroxypropyl)hydroxylamine (HPHA).

Styrene is typically processed at temperatures between 95° and 125° C. The compositions of the present invention are effective at inhibiting polymerization of styrene over this range of temperatures.

The total amount of benzoquinone derivative and hydroxylamine compound used in the methods of the present invention is that amount which is sufficient to inhibit polymerization and will vary according to the conditions under which the vinyl aromatic monomer is being processed and exposed to high temperatures. At higher processing temperatures and higher monomer contamination, larger amounts of the polymerization inhibiting composition are generally required.

For purposes of the present invention, the term "effective inhibiting amount" is defined as that amount of composition which is effective at inhibiting polymerization. Preferably, the effective amount of the inventive composition ranges from about 1 part to about 10,000 parts per million parts monomer. More preferably, the effective amount ranges from about 100 parts to about 2000 parts per million parts monomer.

The weight ratio of benzoquinone derivative compound to hydroxyl-amine compound ranges from about 1:9 to 9:1 with a range of about 1 to 1 preferred.

The compositions of the present invention can be added to the vinyl aromatic monomer by any conventional method at any point along the processing system, either as separate and individual ingredients or as a combination of ingredients. Preferably, the compositions are prepared as a single treatment composition before addition to the vinyl aromatic monomer.

The compositions of the present invention may be added to the vinyl aromatic monomer as either a dispersion or as a solution using a suitable liquid carrier or solvent. Any solvent that is compatible with the individual ingredients of the composition and the vinyl aromatic monomer may be employed.

Accordingly, it is possible therefore to produce a more effective vinyl aromatic monomer polymerization inhibiting treatment than is obtained by the use of either compound alone when measured at comparable treatment levels. This synergism or enhanced activity allows for the concentration of each of the compounds to be lowered and the total quantity of polymerization inhibitor required, particularly at higher processing temperatures, may be lowered.

The preferred inventive embodiment of the composition comprises t-butylbenzoquinone or N,N-dimethylindoaniline (phenol blue) and bis(hydroxypropyl)hydroxylamine.

EXAMPLES

The invention will now be further described with reference to a number of specific examples which are to be regarded solely as illustrative, and not as restricting the scope of the invention.

A reflux test was performed under argon. Freshly distilled styrene (70 mL) with the designated amount of inhibitor was placed in a 100 mL flask. The solution was purged with argon for 30 minutes and then the liquid was heated to 100° C. with a heating mantel. Argon sparging continued throughout the test. Samples were removed every half hour for 2.5 hours and poured into 50 mL of methanol. The resulting polymer was filtered, dried overnight and weighed. Tert butylhydroquinone was oxidized with ferric chloride to give the corresponding tert-butylbenzoquinone (t-butyl BQ) which was used in this testing without purification. The results of this testing are reported in Table I.

TABLE I

Styrene Reflux Test Under Argon
100 ppm Active Treatments

| Time (min) | Control % Polymer Formed | PB/HPHA % Polymer Formed | t-butyl BQ/HPHA % Polymer Formed |
|---|---|---|---|
| 30 | 1.10 | 0.02 | 0.01 |
| 60 | 2.26 | 0.02 | 0.02 |
| 90 | 3.69 | 0.04 | 0.02 |
| 120 | 4.80 | 0.07 | 0.04 |
| 150 | 6.00 | 0.09 | 0.09 |

PB is phenol blue (N,N-dimethylindoaniline)
t-butyl BQ is tert-butylbenzoquinone
HPHA is N,N-bis(hydroxypropyl)hydroxylamine A static test in styrene was also performed. Freshly distilled styrene (5 mL) with the designated amount of inhibitor was placed into a 10 mL test tube and closed with a septa. The solution was purged with argon for 3 minutes and then the liquid was heated in an oil bath at 100° C. for 2 hours. Test tubes were cooled in an icebath for 15 minutes and poured into 45 mL of methanol. The resulting polymer was filtered, dried overnight, and weighed. The results of this testing are reported in Table II.

TABLE II

Styrene Static Test Under Argon

| Treatment | Dosage (ppm active) | Percent Polymer Formed |
|---|---|---|
| Control | — | 4.22 |
| PB | 50 | 2.97 |
| HPHA | 50 | 2.84 |
| PB/HPHA | 50/50 | 0.60 |
| t-butyl BQ | 50 | 2.24 |
| t-butyl BQ/HPHA | 50/50 | 0.02 |

PB is phenol blue (N,N-dimethylindoaniline)
HPHA is bis(hydroxypropyl)hydroxylamine
t-butyl BQ is tert-butylbenzoquinone The results presented in Tables I and II demonstrate the effectiveness of the inventive compositions at inhibiting styrene polymerization and the particular synergy demonstrated by the compositions over that demonstrated by each individual component.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what we claim is:

1. A vinyl aromatic monomer polymerization inhibiting composition comprising a benzoquinone derivative having the formula:

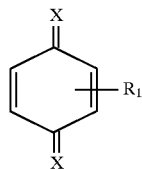

wherein X is N-R or O; R is hydrogen, phenyl, or a $C_1$ to $C_7$ alkyl and $R_1$ is a $C_1$ to $C_7$ alkyl and a hydroxylamine compound is a weight ratio of about 1:9 to 9:1.

2. The composition as claimed in claim 1 wherein said benzoquinone derivative is selected from the group consisting of tert-butylbenzoquinone and N,N-dimethylindoaniline.

3. The composition as claimed in claim 1 wherein said hydroxylamine compound has the formula

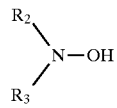

wherein $R_2$ and $R_3$ are the same or different and are hydrogen, alkyl, aryl, alkaryl, aralkyl, or hydroxyalkyl having about three to about twenty carbon atoms.

4. The composition as claimed in claim 3 wherein said hydroxylamine compound is bis(hydroxypropyl) hydroxylamine.

5. The composition as claimed in claim 1 further comprising a vinyl aromatic monomer.

* * * * *